United States Patent
Slater et al.

[11] Patent Number: 6,080,099
[45] Date of Patent: Jun. 27, 2000

[54] RADIOACTIVE THERAPEUTIC SEEDS

[75] Inventors: Charles R. Slater, Fort Lauderdale;
Scott L. Jahrmarkt, Miami Beach;
Scott T. Smith, Miami, all of Fla.

[73] Assignee: Syntheon, LLC, Miami, Fla.

[21] Appl. No.: 09/133,081

[22] Filed: Aug. 12, 1998

[51] Int. Cl.[7] .................................................. A61N 5/00
[52] U.S. Cl. ..................................................... 600/8
[58] Field of Search ............................................ 600/1–8

[56] References Cited

U.S. PATENT DOCUMENTS

| | | | |
|---|---|---|---|
| 1,954,868 | 4/1934 | Fakia et al. .................................. | 600/8 |
| 3,351,049 | 11/1967 | Lawrence .................................. | 128/1.2 |
| 4,323,055 | 4/1982 | Kubiatowicz ............................. | 128/1.2 |
| 4,702,228 | 10/1987 | Russell, Jr. et al. ...................... | 128/1.2 |
| 4,784,116 | 11/1988 | Russell, Jr. et al. ...................... | 128/1.2 |
| 4,815,449 | 3/1989 | Horowitz ................................... | 600/8 |
| 4,891,165 | 1/1990 | Suthanthiran ........................... | 252/633 |
| 5,176,617 | 1/1993 | Fischell et al. ........................... | 600/3 |
| 5,342,283 | 8/1994 | Good ......................................... | 600/8 |
| 5,405,309 | 4/1995 | Carden, Jr. ................................ | 600/3 |
| 5,713,828 | 2/1998 | Coniglione ................................ | 600/7 |

*Primary Examiner*—John P. Lacyk
*Attorney, Agent, or Firm*—David P. Gordon; David S. Jacobson; Thomas A. Gallagher

[57] ABSTRACT

Radioactive therapeutic seeds include a substantially cylindrical capsule containing a radioactive isotope and, preferably, a radiopaque marker. According to one embodiment, the capsule is made of titanium or stainless steel, the isotope is deposited on the surface of a hollow cylinder and a titanium or stainless steel tube is disposed inside the hollow cylinder. The capsule is sealed by swaging the end of the capsule against the inner tube and welding the swaged end and tube. The inner tube facilitates swaging and protects the contents of the capsule from the heat of welding. In alternate embodiments, a radiopaque marker is disposed inside the inner tube or the cylinder bearing the radioisotope is radiopaque. According to other embodiments, a gripping stem is installed on one or both ends of a capsule, a capsule is made of very thin material with rotary swaged ends welded shut and a supporting structure inside the capsule, a meltable isotope mixture is used to coat the interior of a capsule, a capsule is assembled from two halves which are placed over an interior tube and the halves are butt welded, a capsule is made of a borosilicate or elemental silicon glass tube with ends melted to seal the capsule. Bioabsorbable spacers are provided for use with seeds having gripping/linking stems so that seeds are linked together.

29 Claims, 5 Drawing Sheets

RADIOACTIVE THERAPEUTIC SEEDS

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they must be relatively small, approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy. Fourth, the protective package and the radiopaque marker preferably do not cast "shadows" in the irradiation pattern of the isotope. Fifth, the isotope should be evenly distributed within the protective package so as to avoid any "hot spots" of radiation.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent, which issued in 1967, describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which do not absorb X-rays. The isotope is coated on a rod shaped carrier made of similar X-ray transparent (e.g. low Z) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at/around the treatment site.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds results in large beads of shell material at the ends of the seeds. These beads substantially shield radiation thereby casting shadows in the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfitted the total side wall thickness of the assembled capsule is approximately equal to the end wall thickness.

Other improvements in radioactive therapeutic seeds are disclosed in U.S. Pat. No. 5,405,309 which concerns a safe isotopically pure Pd-103 seed, and U.S. Pat. No. 5,713,828 which discloses a hollow tube seed which can be implanted with suture material.

Despite the fact that radioactive therapeutic seeds have been in use for over thirty years and despite the several significant improvements made in these seeds, many concerns still exist regarding their design and construction.

While significant attention has been given to the methods by which a cylindrical seed capsule is sealed, it is still difficult to seal the ends of such a small cylindrical capsule without adversely affecting the functionality of the seed. For example, most of the proposed solutions to the end shadow problem of the Lawrence type seed are difficult to implement. The seeds are manually assembled under a microscope and fitting small pieces together is always difficult. Moreover, given the size of the seeds, it is very difficult to perform any welding of the capsules without adversely affecting the contents in some way.

While it is generally considered desirable that the seed have an isotropic radiation pattern, there are several situations where this may be a disadvantage. For example, in prostrate cancer therapy it is often necessary to place seeds close to the urethra. Irradiation of the urethra can cause incontinence. Thus, in these procedures, it would be desirable to shield the urethra from radiation.

The radioactive therapeutic seeds are typically deployed by injection through a hollow needle into soft tissue. Whereas the Lawrence type seeds appear to have relatively smooth ends, the designs intended to avoid the disadvantages of the Lawrence-type seeds often present end surfaces which would impede movement of the seed through tissue during deployment.

Since the seeds are designed to contain isotopes with relatively short half lives, they are most often not removed from the body. Consequently, the seeds are not designed for easy removal and they are not designed for any type of manipulation after they are deployed.

SUMMARY OF THE INVENTION

It is therefore an object of the invention to provide radioactive therapeutic seeds which are easy to manufacture.

It is also an object of the invention to provide radioactive therapeutic seeds which have smooth ends.

It is another object of the invention to provide radioactive therapeutic seeds which have sealed ends which do not significantly interfere with the irradiation pattern of the seed.

It is still another object of the invention to provide radioactive therapeutic seeds which present a controllable/directional irradiation pattern.

It is another object of the invention to provide radioactive therapeutic seeds which have a structure which permits easy manipulation after they are implanted.

It is also an object of the invention to provide methods of manufacturing radioactive therapeutic seeds which achieve the aforementioned objects.

In accord with these objects which will be discussed in detail below, the radioactive therapeutic seeds of the present invention include a substantially cylindrical capsule containing a radioactive isotope and, preferably, a radiopaque marker.

According to a first embodiment of the invention, the isotope is deposited on the surface of a hollow cylinder, a titanium or stainless steel tube is disposed inside the hollow cylinder and the hollow cylinder and tube are disposed inside a capsule also made of titanium or stainless steel. The capsule is sealed by swaging the end of the capsule against the inner tube and welding the swaged end and tube. One end of the capsule may be pre-sealed by swaging or the capsule may be otherwise manufactured so that it has only one open end. If the capsule is manufactured with two open ends, both ends are closed in the same manner: i.e., by swaging the capsule against the inner tube and welding. The inner tube facilitates swaging and protects the contents of the capsule from the heat of welding. According to one alternate embodiment, the cylinder bearing the isotope is radiotransparent and a radiopaque marker is disposed inside the inner tube. According to another alternate embodiment, the cylinder bearing the radioisotope is radiopaque and no other marker is placed in the capsule. As used herein, the terms "radiotransparent", "radiotranslucent", and "low Z material" are used interchangeably.

According to a second embodiment of the invention, a gripping stem is formed on one or both ends of the capsule. The stem(s) is grippable by an instrument so that the seed may be axially oriented and/or moved or removed. In this embodiment, an anisotropic radiation pattern may be provided and the seed deployed so that the radiation pattern is directed in a particular direction. Directionality is achieved by dimensions of the isotope carrier, coating only portions of the carrier with isotope, or by coating portions of the capsule with a radiopaque material.

According to a third embodiment, the capsule tube is made of very thin titanium or stainless steel with rotary swaged ends welded shut. Since the wall thickness is very thin (approximately 0.001 or 0.002 inches), a supporting structure of aluminum or other radiotransparent material is placed inside the capsule and the isotope bearing structure is placed inside the supporting structure. The isotope bearing structure may be silver or gold or another radiopaque material which is coated with the isotope.

According to a fourth embodiment of the invention, a meltable isotope mixture (such as a monomer or polymer) is deposited inside a capsule, the capsule is sealed and the mixture is melted while the capsule is agitated so that the isotope mixture coats the interior of the capsule.

According to a fifth embodiment of the invention, the capsule is assembled from two halves which are placed over an interior tube made of aluminum or other radiotransparent material. The capsule halves are butt welded while the aluminum inner tube holds the halves together and dissipates the welding heat.

According to a sixth embodiment of the invention, the capsule is made of a borosilicate or elemental silicon glass tube with ends melted to seal the capsule.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
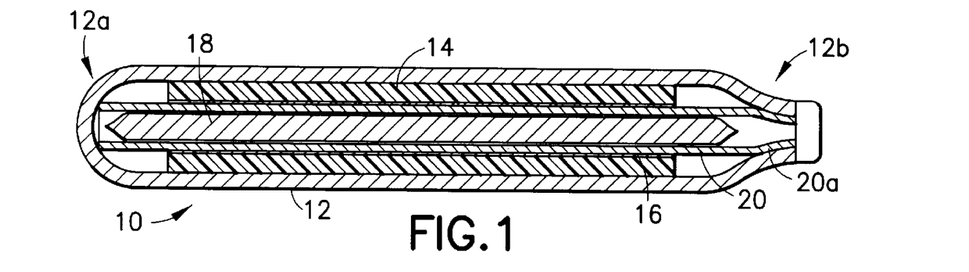
FIG. 1 is an enlarged schematic longitudinal section of a radioactive therapeutic seed according to a first embodiment of the invention.

Referring now to FIG. 1, a radioactive therapeutic seed 10, according to a first embodiment of the invention, includes a radio transparent/translucent (low Z) capsule 12, an isotope carrier body 14 bearing a radioactive coating 16, a radiopaque (high Z) marker 18, and a low Z material inner tube 20. The capsule 12 and the inner tube 20 are made of the same material and are preferably titanium or stainless steel; the carrier body 14 is a hollow plastic cylinder (i.e. low Z material); and the radiopaque marker 18 is a silver or other high Z wire. The radioactive coating 16 is preferably I-125 which is coated on the interior of the plastic tube. According to this embodiment of the invention, one end 12a of the capsule 12 is formed closed as a deep drawn tube and the other end 12b is closed during the assembly of the seed 10. The inner tube 20 is inserted into the capsule 12; the marker 18 is inserted into the inner tube 20; and the cylinder 14 is located in the annular space defined by the tube 20 in the capsule 12. According to this embodiment, the capsule 12 is sealed by swaging the end 12b of the capsule against the end 20a of the inner tube 20 and then welding the swaged ends 12b and 20a. The inner tube 20 facilitates the swaging process and dissipates the heat of welding, thereby maintaining the integrity of the seed. A first alternative to the embodiment of FIG. 1 includes a carrier body 14 of high Z material having an outer surface coated with radioactive material. According to this alternative, the marker 18 may be omitted.

Figure 2:
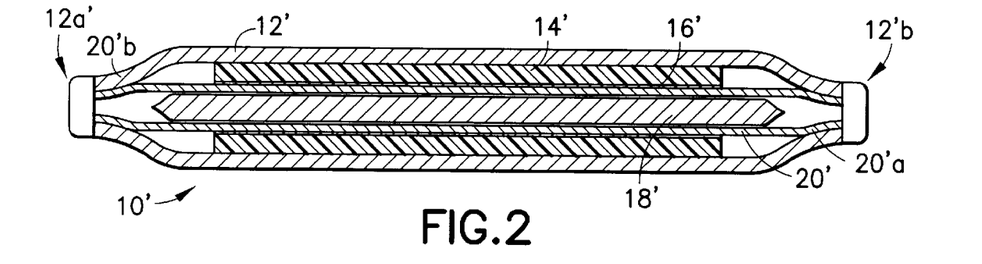
FIG. 2 is a view similar to FIG. 1 of a first alternate first embodiment of the invention.

FIG. 2 shows a second alternate first embodiment of a radioactive therapeutic seed 10' where similar reference numerals refer to similar components and features. According to this embodiment, both ends 12'a and 12'b of the capsule 12 are sealed by swaging and by welding the ends of the capsule.

Figure 2A:
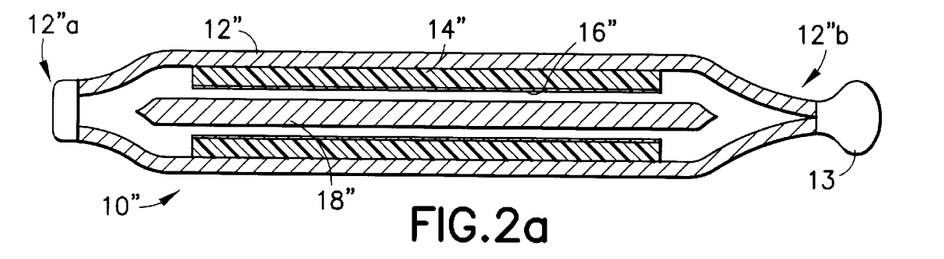
FIG. 2a is a view similar to FIG. 2 of a second alternate first embodiment of the invention.

FIG. 2a shows a third alternate first embodiment of a radioactive therapeutic seed 10" where similar reference numerals refer to similar components and features. According to this embodiment, the end 12"a is welded before the carrier body 14" is installed. After the carrier body is installed, the end 12"b is concavely swaged far enough away from the carrier body that it can be welded without affecting the carrier body. Due to this type of swaging of the end 12"b, the inner tube (20 in FIG. 1) is not needed to protect the contents of the capsule from welding heat. Moreover, the welded end 12"b may be formed to be used as a gripping/linking structure 13 as described below.

Figure 3:
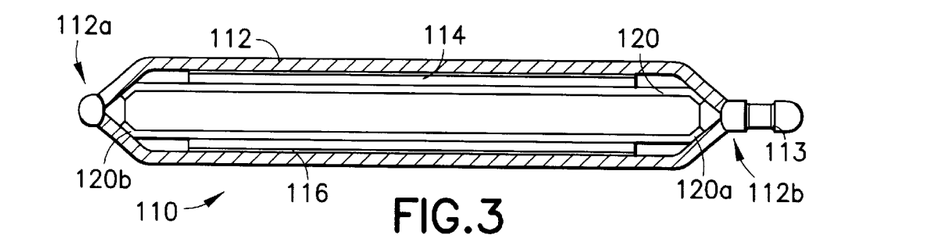
FIG. 3 is an enlarged schematic longitudinal section of a radioactive therapeutic seed according to a second embodiment of the invention.

Turning now to FIG. 3, another embodiment of a radioactive therapeutic seed 110 is similar to the seed 10 described above. According to this embodiment, the cylinder 114 bearing the isotope 116 is made of a high Z material (e.g. silver or gold) and no other marker is placed in the capsule. In addition, the inner tube 120 is shorter than the capsule 112 so that the swaged and welded ends 112a, 112b of the capsule 112 are not welded to the ends 120b, 120a of the tube 120. Those skilled in the art will appreciate that the tube 120 may be replaced with a solid rod as suggested by the shading in FIG. 3. Preferably, the fit between the cylinder 114 and the capsule 112 is relatively loose, but the fit between the cylinder 114 and the tube 120 is relatively tight to act as a holding post so that the cylinder 114 does not move around during swaging/welding.

Figure 4:
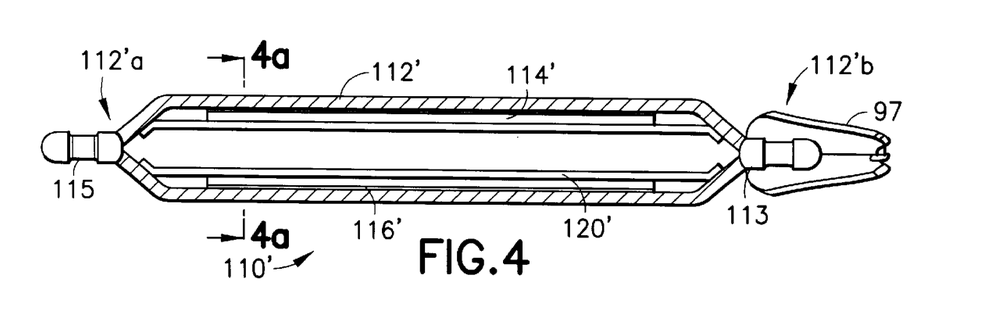
FIG. 4 is a view similar to FIG. 3 of an alternate second embodiment of the invention.

FIG. 3 also illustrates the gripping stem 113 as another feature of the invention. The gripping stem 113 is welded to (or formed from) the end 112b of the capsule 112. The stem 113 is grippable by a grasping instrument 97 as shown in FIG. 4 which illustrates an alternate embodiment of the seed 110'. The seed 110' of FIG. 4 is substantially identical to the seed 110 but for the provision of two gripping stems 113, 115, one at each end of the capsule 112'. The stem(s) allow(s) the seed to be axially oriented and/or moved or removed. In this embodiment, an anisotropic radiation pattern may be provided and the seed deployed so that the radiation pattern is directed in a particular direction.

It will be noticed that in FIGS. 1 and 2, the radioactive material 16, 16' is coated on the inner surface of the carrier 14, 14' whereas in FIG. 3, the material 116 is on the outer surface of the carrier 114. It is presently preferred that the material be coated on an inner surface so that it does not rub off during assembly of the seed.

Figure 4A:
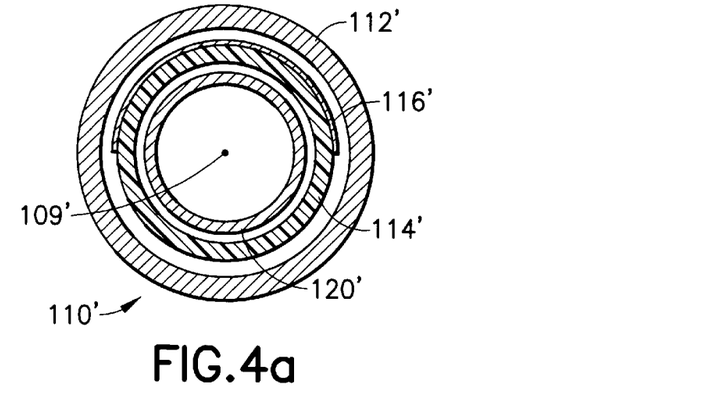
FIG. 4a is a cross sectional view taken along line 4a—4a of FIG. 4 illustrating a first embodiment of a directional seed.
Figure 4B:
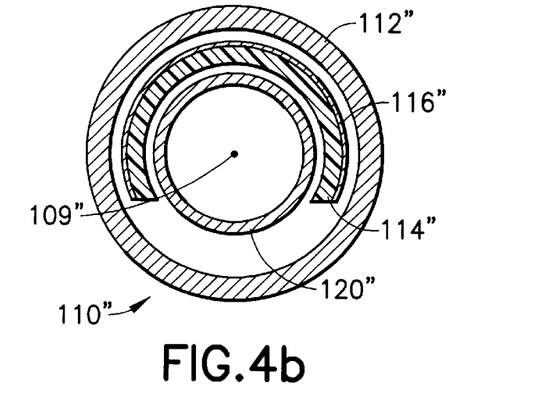
FIG. 4b is a view similar to FIG. 4a illustrating a second embodiment of a directional seed.
Figure 4C:
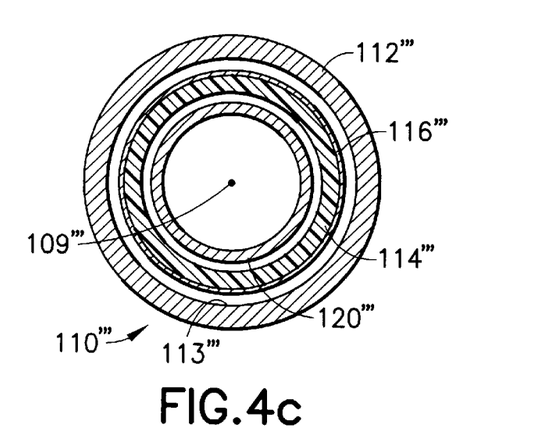
FIG. 4c is a view similar to FIG. 4a illustrating a third embodiment of a directional seed.

FIGS. 4a through 4c illustrate different ways in which the radiation pattern of a seed according to the invention may be made anisotropic. According to the embodiment shown in FIG. 4a, radioactive isotope 116' is coated only on a portion, e.g. 180° of the outer cylindrical surface, of the carrier body 114'. This results in directing the radiation pattern relative to the longitudinal axis 109' of the seed 110'. It will be appreciated that the directionality of the radiation pattern can range from >0° to <360°. According to the embodiment shown in FIG. 4b, the carrier body 114" is less than a full cylinder, such as an angular (e.g. 240°) segment of a cylinder. This results in a radiation pattern of approximately 240°+ about the longitudinal axis 109" of the seed 110". According to the embodiment shown in FIG. 4c, the carrier body 114''' is completely coated with isotope 116''', but a portion 113''' of the seed capsule 112''' is radiopaque, e.g. coated with silver or gold either inside or outside the capsule. This results in a radiation pattern of approximately 180°+ about the longitudinal axis 109''' of the seed 110'''. It will be appreciated that the radiation patterns produced by these seeds may be accurately directed by rotating the seeds with the gripping stems 113, 115 shown in FIGS. 3 and 4.

Figure 5:
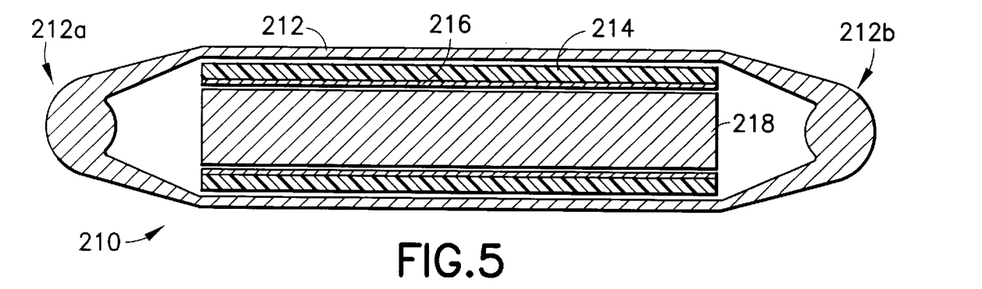
FIG. 5 is an enlarged schematic longitudinal section of a radioactive therapeutic seed according to a third embodiment of the invention.

Referring now to FIG. 5, a radioactive therapeutic seed 210 includes a capsule 212, a cylindrical carrier body 214 bearing a radioactive coating 216, and a radiopaque marker 218. According to this embodiment, the capsule 212 is made of very thin (e.g. 0.001 or 0.002 inch) titanium or stainless steel with rotary swaged ends 212a, 212b welded shut.

Figure 6:
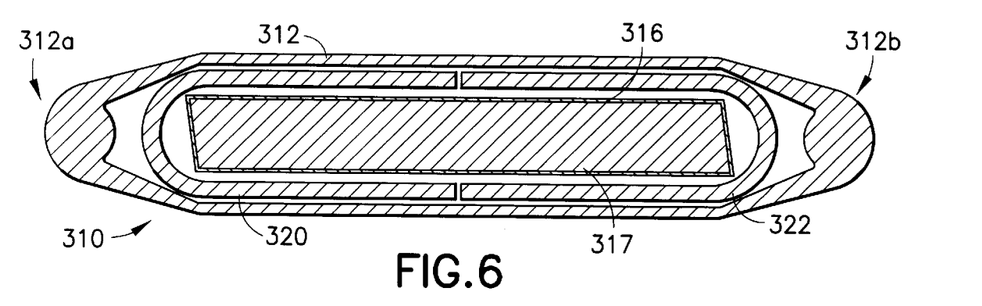
FIG. 6 is a view similar to FIG. 5 of a preferred version of the third embodiment of the invention.

The embodiment of FIG. 5 is preferably modified as shown in FIG. 6 in order to provide support for the very thin (approximately 0.002 inches) capsule wall. Accordingly, the radioactive therapeutic seed 310 includes a thin walled capsule 312, a cylindrical radiopaque (e.g. silver or gold) carrier body 317 bearing a radioactive coating 316, and a pair of radiotransparent (e.g. aluminum) supporting/protecting members 320, 322. The supporting/protecting members protect the capsule and its contents without absorbing any significant amount of radiation. This thin wall seed has a total maximum radiation absorption of approximately 15% whereas the state of the art seeds have a minimum absorption of approximately 21%.

Figure 7:
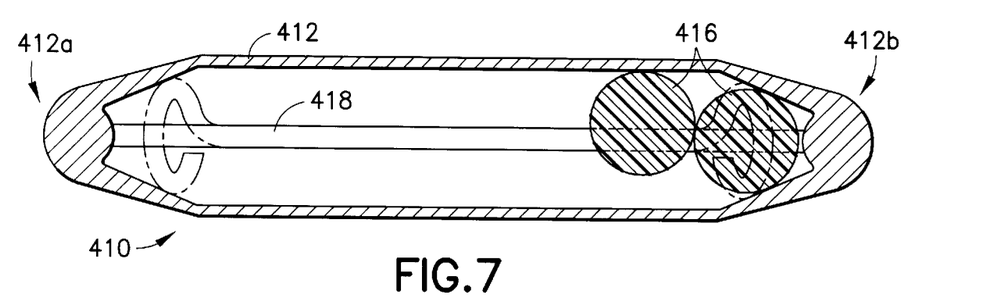
FIGS. 7 and 8 are enlarged schematic longitudinal sections illustrating a fourth embodiment of the invention.
Figure 8:
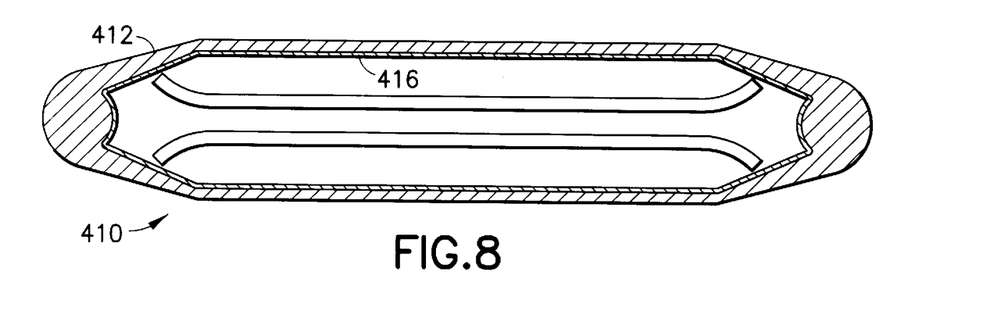

Turning now to FIGS. 7 and 8, a radioactive therapeutic seed 410 includes a capsule 412 and an isotope 416. According to this embodiment, a meltable isotope mixture 416 (e.g. a mixture of I-125 and a polymer such as polyurethane) is deposited inside the capsule 412 as shown in FIG. 7. The capsule 412 is sealed and the mixture is melted while the capsule is agitated so that the isotope mixture 416 coats the interior of the capsule as shown in FIG. 8. Prior to depositing the mixture 416, and prior to sealing either end 412a, 412b, a high Z material marker wire 418 is preferably inserted into the capsule and one end, e.g. 412a, is welded closed and to the wire. Alternatively, a wire with flared ends or a self-centering form is placed into the capsule before depositing the mixture 416.

Figure 9:
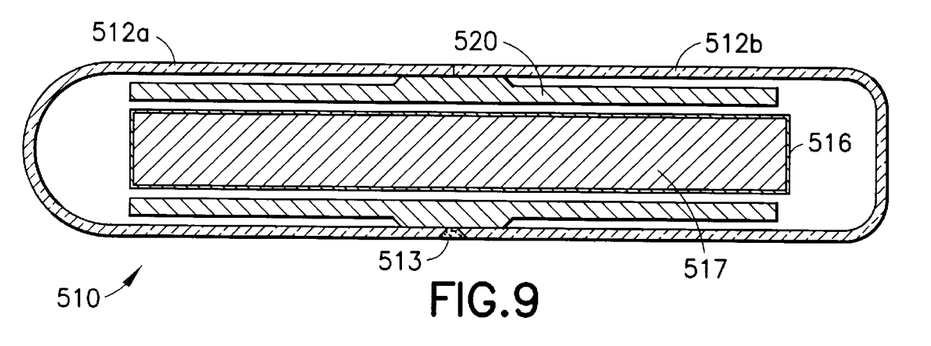
FIG. 9 is an enlarged schematic longitudinal section of a radioactive therapeutic seed according to a fifth embodiment of the invention.

According to another embodiment, shown in FIG. 9, a radioactive therapeutic seed 510 includes a titanium or stainless steel capsule which is assembled from two halves 512a, 512b which are placed over an interior tube 520 made of aluminum or other radiotransparent/radiotranslucent or low Z material. The capsule halves 512a, 512b are butt welded at 513 while the aluminum inner tube 520 holds the halves together and dissipates the welding heat. A radiopaque rod 517 coated with an isotope 516 is disposed inside the capsule during assembly prior to welding.

Figure 10:
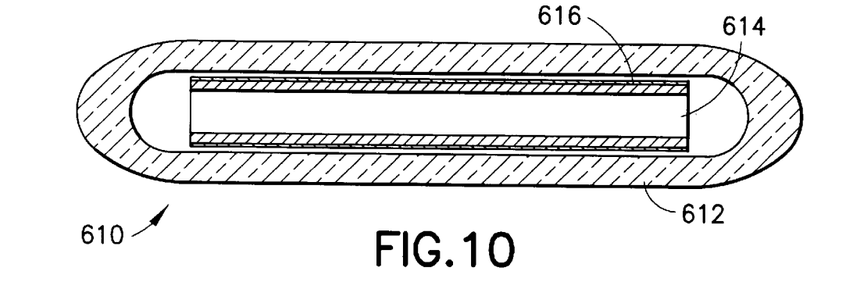
FIGS. 10 and 11 are enlarged schematic longitudinal sections illustrating a sixth embodiment of the invention.
Figure 11:
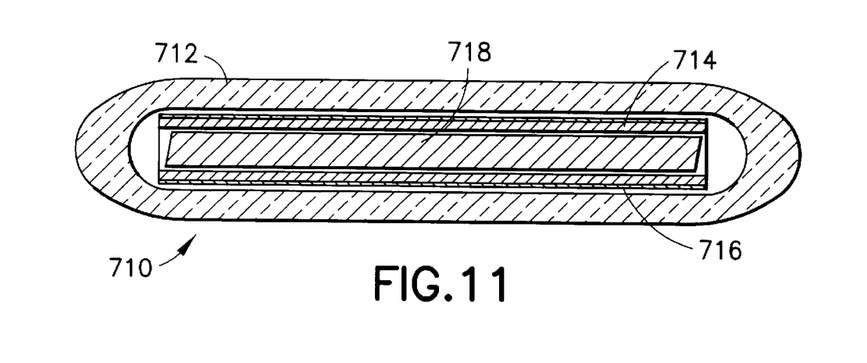

According to still another embodiment, shown in FIG. 10, a radioactive therapeutic seed 610 includes a capsule 612 made of a borosilicate or elemental silicon glass tube with ends melted to seal the capsule. As shown in FIG. 10, a radiopaque cylinder 614 coated with an isotope 616 is disposed in the capsule 612 before it is sealed. An alternate version of this seed is shown in FIG. 11. The seed 710 utilizes a capsule 712 made of a borosilicate or elemental silicon glass tube with ends melted. In this alternate version, a radiopaque marker 718 is disposed inside a radiotransparent cylinder 714 which is coated with isotope 716. Those skilled in the art will appreciate that the seeds of FIGS. 9 and 10 could be made of a high temperature polymer in lieu of borosilicate or elemental silicon glass.

Figure 12:
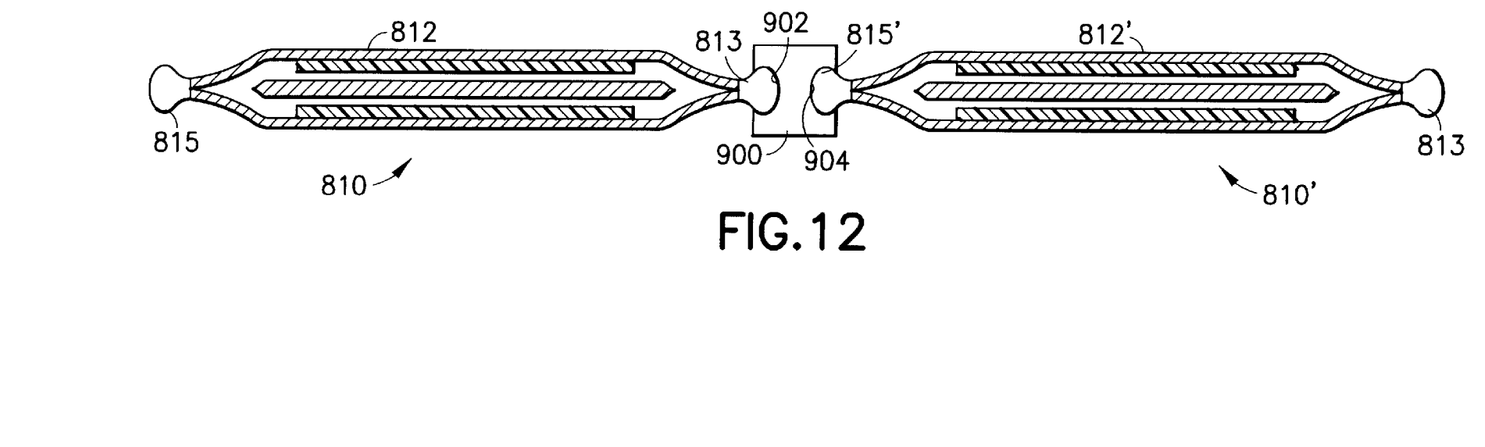
FIG. 12 is an enlarged schematic longitudinal section of an embodiment of the invention in conjunction with a bioabsorbable spacer.

Referring now to FIG. 12, another aspect of the invention is illustrated with reference to seeds 810 and 810' which are substantially identical to each other and which are representative of the embodiments of FIGS. 2–4 described above. In particular, each of the seeds has a pair of gripping "stems" 813, 815, 813', 815'. As mentioned above, these gripping elements may be formed from the solder or weldment used to seal the capsules 812, 812'. According to the invention, seeds formed with gripping ends may be used in conjunction with a special bioabsorbable spacer 900. The bioabsorbable spacer 900 is provided with cavities 902, 904 at opposite ends thereof. These cavities are dimensioned to interlock with the gripping stems 813, 815', etc. as shown in FIG. 12. According to the invention, seeds are linked together prior to loading them into an injection needle so that when they are deployed, they will remain connected to each other. Spacers 900 of different length are provided so that the practitioner may determine in advance of the procedure how far apart adjacent seeds will be spaced.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. It will therefore be appreciated by those skilled in the art that yet other modifications could be made to the provided invention without deviating from its spirit and scope as so claimed.

What is claimed is:
1. A radioactive therapeutic seed, comprising:
   a) a biocompatible capsule;
   b) a carrier structure carrying a radioactive isotope, said carrier structure disposed in said capsule; and
   c) a carrier protective structure disposed in said capsule.
2. A seed according to claim 1, wherein:
   said carrier protective structure is a tube and said carrier structure is a hollow cylinder surrounding said tube.
3. A seed according to claim 2, further comprising:
   d) a radiopaque marker disposed inside said tube.
4. A seed according to claim 1, wherein:
   said carrier structure is radiopaque.
5. A seed according to claim 1, further comprising:
   d) a first gripping stem coupled to one end of said capsule.
6. A seed according to claim 5, further comprising:
   e) a second gripping stem coupled to another end of said capsule.
7. A seed according to claim 1, wherein:
   said carrier protective structure is a pair of tubes, each having an open end and a closed end, said open ends of said tubes facing each other.
8. A seed according to claim 1, wherein:
   said carrier protective structure is a tube and said carrier structure is disposed inside said tube.
9. A seed according to claim 7, wherein:
   said capsule is formed from two parts which are butt welded together.
10. A seed according to claim 9, wherein:
    said two parts are substantially the same size.
11. A seed according to claim 1, wherein:
    said capsule has a swaged end and said carrier protective structure underlies said swaged end.
12. A seed according to claim 11, wherein:
    said swaged end is welded and said carrier protective structure dissipates welding heat.
13. A seed according to claim 12, wherein:
    said swaged end is welded to said carrier protective structure.
14. A seed according to claim 1, wherein:
    said carrier protective structure is disposed between said capsule and said carrier structure.
15. A seed according to claim 1, wherein:
    said carrier structure is disposed between said carrier protective structure and said capsule.
16. A radioactive therapeutic seed system, comprising:
   a) at least two seeds, each seed comprising
      i) a biocompatible capsule having a first end and a second end, one of said first and second ends having a linking structure, and
      ii) a radioactive isotope disposed in said capsule; and
   b) a linking member adapted to couple said linking structure of one seed to said linking structure of another seed, wherein
      said linking member is bioabsorbable.
17. A radioactive therapeutic seed, comprising:
   a) a biocompatible capsule having a first end and a second end; and
   b) a radioactive isotope disposed in said capsule, wherein one of said first and second ends has a linking/gripping structure whereby said seed being adapted to be manipulated with an instrument or linked to another seed, wherein said linking member is bioabsorbable.

18. A radioactive therapeutic seed, comprising:

a) a biocompatible capsule having a longitudinal axis; and b) a radioactive isotope disposed in said capsule, wherein said seed is adapted to provide a radiation pattern of less than 360° about said longitudinal axis.

19. A seed according to claim 18, further comprising:

c) a cylinder which carries said isotope, wherein said isotope is disposed on the outer surface of said cylinder covering less than 360° of said cylindrical structure.

20. A seed according to claim 18, wherein:

a portion of said capsule is radiopaque.

21. A seed according to claim 18, further comprising:

c) a cylinder section of less than 360°, said cylinder section carrying said isotope.

22. A radioactive therapeutic seed, comprising:

a) a biocompatible capsule having an interior surface and an exterior surface; and b) a radioactive isotope coating said interior surface of said capsule.

23. A seed according to claim 22, further comprising:

c) a radiopaque marker structure disposed inside said capsule.

24. A radioactive therapeutic seed, comprising:

a) a radiotransparent biocompatible capsule made of an element selected from the group consisting of borosilicate and elemental silicon glass; and b) a carrier structure carrying a radioactive isotope, said carrier structure disposed in said capsule.

25. A seed according to claim 24, further comprising:

c) a radiopaque marker disposed inside said carrier structure.

26. A seed according to claim 24, wherein:

said carrier structure is radiopaque.

27. A radioactive therapeutic seed, comprising:

a) a biocompatible capsule having a first end, a second end, and an outer surface; and b) a radioactive isotope disposed in said capsule, wherein one of said first end and said second end is rotary swaged concavely relative to said outer surface and welded.

28. A radioactive therapeutic seed system, comprising:

a) at least two seeds, each seed comprising
   i) a biocompatible capsule having a first end and a second end, one of said first and second ends having a linking structure, and
   ii) a radioactive isotope disposed in said capsule; and b) a linking member adapted to couple said linking structure of one seed to said linking structure of another seed such that said seeds are held relatively immovable to each other under longitudinal compression and longitudinal extension.

29. A radioactive therapeutic seed, comprising:

a) a biocompatible capsule having a first end and a second end; and b) a radioactive isotope disposed in said capsule, wherein one of said first and second ends has a linking/gripping structure whereby said seed being adapted to be manipulated with an instrument or linked to another seed such that said linking/gripping is resistant to both tension and compression.

* * * * *